United States Patent [19]

Benedict et al.

[11] Patent Number: 5,283,617
[45] Date of Patent: Feb. 1, 1994

[54] DEVELOPMENT APPARATUS EMPLOYING MAGNETIC FIELD SHAPERS

[75] Inventors: Lawrence R. Benedict, Rushville; Gary A. Denton, Webster; Francisco Zirilli, Walworth; Jorge A. Alvarez, Rochester, all of N.Y.

[73] Assignee: Xerox Corporation, Stamford, Conn.

[21] Appl. No.: 942,866

[22] Filed: Sep. 10, 1992

Related U.S. Application Data

[63] Continuation-in-part of Ser. No. 814,171, Dec. 30, 1991, which is a continuation-in-part of Ser. No. 757,100, Sep. 10, 1991, abandoned.

[51] Int. Cl.5 .......................................... G03G 15/09
[52] U.S. Cl. .................................. 355/253; 118/658; 355/215; 430/122
[58] Field of Search ............... 355/215, 245, 251, 253, 355/259, 269, 296, 297, 298, 305; 118/656, 657, 658, 639; 430/122

[56] References Cited

U.S. PATENT DOCUMENTS

| | | | |
|---|---|---|---|
| 3,807,853 | 4/1974 | Hudson | 355/298 |
| 4,067,018 | 1/1978 | Pond | 118/652 X |
| 4,078,929 | 3/1978 | Gundlach | 96/1.2 |
| 4,260,235 | 4/1981 | Stack | 355/215 |
| 4,292,924 | 10/1981 | Lindblad et al. | 118/658 |
| 4,320,958 | 3/1982 | Fantuzzo | 355/270 |
| 4,378,754 | 4/1983 | Raseuchi et al. | 118/658 |
| 4,439,034 | 3/1984 | Daniels | 118/658 X |
| 4,466,730 | 8/1984 | Jugle | 355/215 |
| 4,517,719 | 5/1985 | Okumura et al. | 29/124 |
| 4,640,808 | 2/1987 | Okumura et al. | 264/46.5 |
| 4,641,946 | 2/1987 | Forbes, II | 355/251 |
| 4,721,661 | 1/1988 | Olson et al. | 118/652 X |
| 4,797,708 | 1/1989 | Kaiske, Jr. et al. | 355/296 |
| 4,811,046 | 3/1989 | May | 355/326 |
| 4,829,338 | 5/1989 | Whittaker et al. | 355/305 |
| 4,833,504 | 5/1989 | Parker et al. | 355/326 |
| 4,878,089 | 10/1989 | Guslits et al. | 355/253 |
| 4,972,231 | 11/1990 | Bares | 355/251 |
| 4,996,538 | 2/1991 | Brecy et al. | 118/657 X |
| 5,052,336 | 10/1991 | Fukuchi | 355/251 X |
| 5,063,412 | 11/1991 | Hirsch | 355/259 |
| 5,138,382 | 8/1992 | Van Duser et al. | 355/215 |
| 5,138,388 | 8/1992 | Kamp et al. | 355/251 |

Primary Examiner—Leo P. Picard
Assistant Examiner—Christopher Horgan

[57] ABSTRACT

An electrophotographic printing machine in which an electrostatic latent image is recorded on a moving photoconductive surface by charging the appropriate areas of the surface to predetermined polarities. The latent image is a developed in a development zone with toners of a preselected color and predetermined polarity which are delivered by magnetic bead carriers. A bead removal device is provided adjacent the surface and downstream from the development zone relative to the movement of the surface. The bead removal device magnetically attracts carrier beads off the photoconductive surface. The beads are then deposited in a sump. A vacuum source is also provided for urging beads into the sump from the surface. The bead removal device comprising a sleeve mounted for rotation in a housing, adjacent the surface. The sleeve has a fixed magnet disposed proximate the surface therein and a shunt disposed generally opposite the magnet to define an attraction zone and a release zone. The vacuum source has a port proximate the release zone for drawing beads thereto and the housing can be ultimately formed to have a large aperture or relatively small aperture to urge beads on and near the photoconductive surface to the small aperture.

14 Claims, 4 Drawing Sheets

DEVELOPMENT APPARATUS EMPLOYING MAGNETIC FIELD SHAPERS

This application is a continuation-in-part of U.S. application Ser. No. 814,171, which was filed on Dec. 30, 1991 which is a continuation-in-part of U.S. application Ser. No. 757,100, filed on Sep. 10, 1991, now abandoned, and assigned to the same assignee as of this application.

This invention relates generally to an electrophotographic printing machine adapted to produce highlight color and monochromatic copies, and more particularly concerns a development system having at least one developer unit which employs ferromagnetic carriers in the delivery of toner to a photoconductive surface and has apparatus for removing ferromagnetic carrier from a photoconductive surface prior to transfer to a copy sheet.

INCORPORATION BY REFERENCE

The following herein are incorporated by reference: U.S. Pat. No. 4,829,338, U.S. Pat. No. 4,811,046, U.S. application Ser. No. 757,100, and U.S. application Ser. No. 814,171.

BACKGROUND OF THE INVENTION

The features of the present invention may be used in the printing arts and more particularly in electrophotographic printing. In the process of electrophotographic printing, a photoconductive surface is charged to a substantially uniform potential. The photoconductive surface is image wise exposed to record an electrostatic latent image corresponding to the informational areas of an original document being reproduced. This records an electrostatic latent image on the photoconductive surface corresponding to the informational areas contained within the original document. Thereafter, a developer material is transported into contact with the electrostatic latent image in a region known as the development zone. Toner paritcles are attracted from carrier granules or bead carriers of the developer material onto the latent image. The resultant toner powder image is then transferred from the photoconductive surface to a copy sheet and permanently affixed thereto. The foregoing generally describes a typical mono-color electrophotographic copying machine.

Recently, electrophotographic printing machines have been developed which produce highlight color copies. A typical highlight color printing machine records successive electrostatic latent images on the photoconductive surface. When combined, thes electrostatic latent images form a total latent image corresponding to the entire original document being reproduced.

One latent image is usually developed with black toner particles. The other latent image is developed with color highlighting toner particles, e.g. red toner particles. These developed toner images are transferred sequentially to the copy sheet to form the color highlighted copy. A color highlight printing machine of this type is a two pass machine.

Single pass highlight color printing machines using tri-level printing have also been developed. Tri-level electrophotographic printing is described in detail in U.S. Pat. No. 4,078,929. As described in this patent, the latent image is developed with toner particles of first and second colors. The toner particles of one of the colors are positively charged and the toner particles of the other color are negatively charged. In one embodiment, the toner particles are supplied by a developer which comprises a mixture of triboelectrically relatively positive and relatively negative carrier beads. The carrier beads support, respectively, the relatively negative and relatively positive toner particles. Such a developer is generally supplied to the charge pattern by cascading it across the imaging surface supporting the charge pattern. In another embodiment, the toner particles are presented to the charge pattern by a pair of magnetic brushes. Each brush supplies a toner of one color and one charge. In yet another embodiment, the development system is biased to about the background voltage. Such biasing results in a developed image of improved color sharpness.

In tri-level electrophotographic printing, the charge on the photoconductive surface is divided in three, rather than two, ways as is the case in mono-color printing. The photoconductive surface is charged, typically to about 900 volts. It is exposed image wise, such that one image corresponding to charged image areas remains at the full potential of 900 volts. The other image, which corresponds to discharged image areas is exposed to discharge the photoconductive surface to its residual potential of typically about 100 volts. The background areas are exposed to reduce the photoconductive surface potential to about halfway between the charged and discharged potentials, (typically about 500 volts). The developer unit arranged to develop the charged image areas, is typically biased to about 600 volts, and the developer unit, arranged to develop the discharged image areas, is biased to about 400 volts.

The single pass nature of this system dictates that the electrostatic latent image pass through the developer units in a serial fashion. When the latent image, which has a high charged image potential region and a low charge image potential region, passes through the first developer unit, arranged to develop the discharged image areas, an extremely high cleaning field potential is established between the electrically biased developer unit and the highly charge image areas of the latent image. This high cleaning field potential attracts developer material from the developer unit onto the highly charged image areas. When this occurs, the highly charged image areas of the electrostatic latent image are locally discharged where developed, and as a result, white spots will be noticeable in the solid area images developed by the second developer unit, which at the present time is black, rendering the prints unacceptable.

This problem was overcome by the invention disclosed in the below-referenced co-pending U.S. application Ser. No. 07/604,269. However, electrostatic forces and adhesion forces within the developer units contribute to a condition where the bead carriers are carried out of the development unit. Bead removal devices (BRDs) are well known and commonly used to pick off any developer carriers which are carried out of the development zone of a development unit.

Generally BRDs operate by generating a strong magnetic field in the area between the photoconductive surface and the BRD to attract free bead carriers to the shell of the BRD. These captured beads are then deposited in a sump or developer receiver as the shell of the BRD is rotated. This arrangement, however, renders release of beads from the BRD more difficult, e.g. gravity and centripetal forces often are insufficient to achieve release of the beads from the magnetic field as the shell of the BRD rotates. That is the strong magnetic field necessary to attract bead carriers from the photoconductive surface to the BRD shell are sufficiently strong around the shell itself to retain some bead carriers as the shell rotates.

As disclosed in U.S. Pat. No. 4,829,338, the magnetic field from the magnet positioned in the shell of the BRD can be directed by use of a ferromagnetic shunt to promote bead removal from the photoconductive surface while enhancing the field between the photoconductive surface and the BRD to attract free beads. Nevertheless, this solution has not overcome all problems associated with BRDs.

Specifically, some bead carriers remain attached to the shell as the shell rotates. These unreleased beads tend to attract additional beads to themselves to form bead chains. These bead chains can span the gap between the BRD and photoconductive surface causing degradation of the image being reproduced. For example, in highlight color electrophotographic printing machines, when bead chains occur in the first discharged developer unit, portions of the second latent image which are contacted by the chains are discharged thereby causing discharge line defects in the finished print.

Also, the arrangement disclosed in U.S. Pat. No. 4,829,338 does not address carrier pickup and carry through in reverse rotation of a BRD. In highlight color electrographic printing machines using magnetic delivery means, monochromatic images are often achieved by disabling one of the developer units. One technique is to reverse the direction of the magnetic brush rollers as disclosed in U.S. Pat. No. 4,811,046 to May, which is incorporated by reference herein. The reversal of the direction of travel of the rollers in the developing units in this case effects a substantial reduction in developer available to effect the charged photoconductive surface. Such reversal of angular travel of the rollers can also be done during warm-up and shut down cycles to remove stray or extraneous developer materials from the developer zone. However, reversed rotation of the rollers is not entirely satisfactory, as some beads are not released and certain other beads are attracted to and attach to the roller. Failure to release the beads, as well as the attraction of additional beads, results, for example, in discharge of portions of the latent image on the photoconductive surface as it passes through a developer unit to a secondary developer unit.

Another problem associated with the use of magnetic carrier beads and toner to form the developer material is the failure to remove substantially all of the beads that are attracted to the photoconductive surface. This problem seems to increase as the speed of the latent image bearing surface increases. Thus, in the effort to improve the output of devices by increasing the speed of the device, it seems that known means for removing excess and unwanted materials from the surface are insufficient. For example, it appears that beads which are smaller than average size or which are fragments or fractured portions of full sized beads tend to be more susceptible to carry past the developer station to the transfer and fusing stations. In any event, as previously mentioned, bead carry through is a significant problem which has deleterious effects upon the quality of prints made by electrophotographic printers employing two part magnetic toner.

Yet another problem associated with the developer rollers is that during ordinary operation some beads fail to release from the developer rollers. When this involves a substantial number of beads, a condition mimicking a low toner condition results. Essentially, empty beads are being transported through the development zone and insufficient toner is delivered to develop the latent image. Optimally, the magnetic field at the release point the of development rollers must be minimized to reduce carry through of 'empty' beads and to prevent carry back of beads in the "reversed" rotating rollers. Further, this must be accomplished without substantially affecting the magnetic field characteristics along the remainder of the rollers which are responsible for bead pickup, bead transport, bead trimming, developing by toner, migration from bead to photoconductive surface and carryout of beads from development zone. Also, the magnetic fields around a BRD housing must be maximized along the interface between the BRD shell and the photoconductive surface and minimized at all other points to afford return of released beads to a sump or reservoir and to impede bead chain formation.

Another vexing problem occurs with electrically biasing the BRD with an alternating current to improve bead attraction. Specifically, the BRD at higher bias levels becomes so attractive that the attracted beads and excess toner fail to release at desired locations. Rather, the formation of bead chains is encouraged, and the aggregation of materials on the BRD severely degrades its performance so that beads and free toner are not attracted to the BRD.

Various techniques have heretobefore been used to develop electrostatic latent images as illustrated by the following disclosures, which may be relevant to certain aspects of the present invention:

U.S. Pat. No. 4,320,958; Patentee: Fantuzzo; Issued: Mar. 23, 1982.

U.S. Pat. No. 4,641,946; Patentee: Forbes II; Issued: Feb. 10, 1987.

U.S. Pat. No. 4,833,504; Patentee: Parker et al.; Issued: May 23, 1989.

Co-pending U.S. application Ser. No. 07/604,269; Applicant: Hogestyn; Filed: Oct. 29, 1990.

U.S. Pat. No. 4,292,924; Patentee: Lindblad et al.; Issued: Oct. 6, 1981.

U.S. Pat. No. 5,063,412; Patentee: Hirsch; Issued: Nov. 5, 1991.

U.S. Pat. No. 4,972,231; Patentee: Bares; Issued: Nov. 20, 1990.

U.S. Pat. No. 4,878,089; Patentee: Guslits et al; Issued: Oct. 31, 1989.

U.S. Pat. No. 4,466,730; Patentee: Jugle, et al.; Issued: Aug. 1, 1984.

U.S. Pat. No. 4,797,708; Patentee: Kasiske, Jr. et al.; Issued: Jan. 10, 1989.

U.S. Pat. No. 5,225,880; Patentee: Shehata et al.; Issued: Jul. 6, 1993.

The relevant portions of the foregoing patents may be briefly summarized as follows:

U.S. Pat. No. 4,320,958 discloses a processing station for an electrophotographic printing which cleans the photoconductive surface and develops an electrostatic latent image recorded thereon. The processing unit uses an indexable magnet positioned interiorly of a rotating tubular sleeve. During development, the magnet is indexed so that a weak magnetic field is generated in the development zone during development. During cleaning, the magnet is indexed to generate a strong magnetic field in the cleaning zone.

U.S. Pat. No. 4,641,946 describes a developer roller having a rotating tubular sleeve with a magnet disposed interiorly thereof. A photoconductive belt is wrapped about a portion of the exterior surface of the sleeve. The magnet generates a radial magnetic field in the development zone which, at the center, may range from 0 gauss to 500 gauss. FIG. 4 shows a radial magnetic field, in the development zone, having a valley of about −185 gauss and twin peaks, each of about −385 gauss.

U.S. Pat. No. 4,833,504 discloses a single pass highlight color electrophotographic printing machine using two developer units. The first developer unit contains developer with black toner. The black toner is driven to the most highly charged areas of the latent image by the electrostatic field between the photoreceptor and developer rolls. The second developer unit contains developer with the highlight color toner. The highlight color toner is urged towards the parts of the latent image at the residual potential, i.e. the discharged region of the latent image, by the electrostatic field between the photoreceptor and the development rolls in the second housing. The magnetic rolls in the second developer unit are constructed such that the radial component of the magnetic force field produces a magnetically free development zone intermediate a charge retentive surface and the magnetic rolls. The developer is moved through the zone magnetically unconstrained and subjects the image developed by the first developer unit to minimal disturbance. In addition, the developer is transported from one magnetic roll to the next.

Co-pending U.S. patent application Ser. No. 07/604,269 describes an electrophotographic printing machine in which an electrostatic latent image is recorded on a photoconductive surface. One portion of the latent image is a discharged area with the other portion of the latent image being a charged area. The discharged image area is developed with toner particles of a first color and polarity by a first developer unit. The first developer unit generates a weak magnetic field in the development zone and a strong magnetic field at the entrance and exit of the development zone. A second developer unit develops the charged image area with toner of a second color and polarity. The colors of the toners are different from one another.

U.S. Pat. No. 4,292,924 discloses a magnetic brush apparatus for cleaning photoconductive surfaces and suggests its application to magnetic brush development mechanisms. The disclosure device has a series of magnetics disposed within a rotating cylindrical sleeve disposed within a cleaning housing. The cleaning housing has an aperture which is proximate a photoconductive surface so that the surface is cleaned as it passes the aperture. The sleeve is provided with field shaping devices at the extreme ends of the cleaning roller so that developer material attracted to the sleeve does not build at the extreme ends of the cylindrical sleeve.

U.S. Pat. No. 5,063,412 discloses an electrophotographic printing machine with a rotating magnetic brush unit having magnetics disposed within the units. The magnetics disposed proximate the photoconductive surface are electromagnetic which are inactivated when developing a latent image and activated to exert a strong field when developer material is to be retained on the sleeve without developing the photoconductive surface.

U.S. Pat. No. 4,972,231 discloses a magnetic brush developer unit having a movable magnet disposed with the rotating portion of the magnetic brush developer. The magnet is movable between an active position away from the exterior wall of the unit and the photoconductive surface to permit development of latent images on the surface and an inactive position closer to the surface which impedes development of any latent images on the surface.

U.S. Pat. No. 4,878,089 discloses a magnetic brush developer station with a magnetic brush for applying developer material to a charge pattern bearing medium.

U.S. Pat. No. 4,466,730 discloses a magnetic brush developer unit having a housing in which a magnetic is disposed within a rotating tubular member for transporting carrier beads with toner adhereing thereto to a photoconductive surface. The area adjacent the tubular member and within the housing has a negative air pressure as air is withdraw from the housing so that airborne toner and toner on the metering blade are attracted to the bottom of the housing.

U.S. Pat. No. 4,797,708 discloses an electrophotographic printing machine with a vacuum slit or air knife positioned adjacent the photoreceptor for picking up large particles off the photoreceptor by aerodynamic drag as it passes within the vacuum flow.

U.S. Pat. No. 5,225,880 also discloses a system for removing agglomerates from a developed image on a photoreceptor in an electrophotographic printing machine.

In accordance with one aspect of the present invention, there is provided an apparatus for developing a latent image in an electrophotographic printing machine of the type having a latent image recorded on a moving charge retentive surface comprising magnetic means, generating a magnetic field, for attracting and moving magnetic carrier beads having toner particles adhering triboelectrically thereto to a development zone proximate to the photoconductive surface so that the latent image attracts toner particles from the carrier beads thereto. The apparatus of the present invention further includes magnetic pick off means positioned adjacent the surface and downstream from the development zone for removing magnetic carrier beads adhering to the surface and vacuum means for removing magnetic carrier beads adhering to said magnetic pick off means generating an aeriform fluid flow to remove magnetic carrier beads adhering to the magnetic pick off means.

In accordance with other aspects of the present invention, this provides an apparatus for developing a latent image recorded on a moving photoconductive surface comprising magnetic means, generating a magnetic field, for attracting and moving magnetic carrier beads having toner particles adhering triboelectrically thereto to a development zone proximate to the photoconductive surface so that the latent image attracts toner particles from the carrier beads thereto. This apparatus also includes combination vacuum and magnetic pick off means positioned adjacent the surface and downstream from the development zone for removing magnetic carrier beads adhering to the surface.

In accordance with yet another aspect of this invention, there is provided a method for developing a latent image recorded on a moving photoconductive surface comprising the steps of generating a magnetic field, for attracting and moving magnetic carrier beads having toner particles adhering triboelectrically thereto to a development zone proximate to the photoconductive surface so that the latent image attracts toner particles from the carrier beads thereto. The method also includes generating a second magnetic field with a magnetic pick off means positioned adjacent the surface and downstream from the development zone for removing magnetic carrier beads adhering to the surface and generating an aeriform fluid flow to remove magnetic carrier beads adhering to the magnetic pick off means.

Other features of the present invention will become apparent as the following description proceeds and upon reference to the drawings, in which:

While the present invention will be described in connection with a preferred embodiment thereof, it will be understood that it is not intended to limit the invention to that embodiment. On the contrary, it is intended to cover all alternatives, modifications, and equivalents as may be included within the spirit and scope of the invention as defined by the appended claims.

Figure 1:
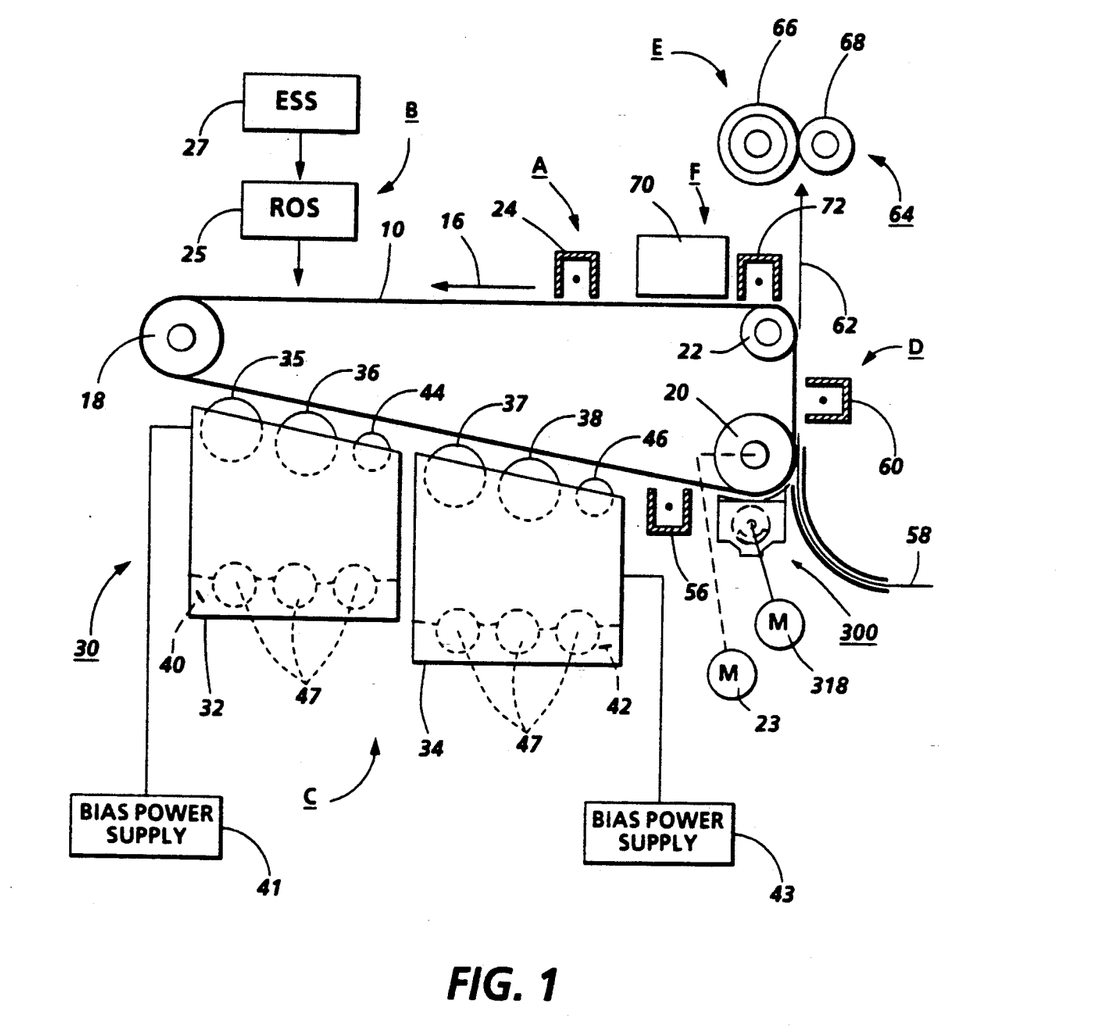
FIG. 1 is a schematic elevational view of an illustrative electrophotographic printing machine incorporating the developer units of the present invention therein.

For a general understanding of the illustrative electrophotographic printing machine incorporating the features of the present invention therein, reference is made to the drawings. In the drawings, like reference numerals have been used throughout to designate identical elements. FIG. 1 schematically depicts the various components of an electrophotographic printing machine incorporating the developer units of the present invention therein. Although the developer units of the present invention are particularly well adapted for use in the illustrative printing machine, it will become evident that these developer units are equally well suited for use in a wide variety of printing machines and are not necessarily limited in their application to the particular embodiments shown herein.

Referring now to FIG. 1, the electrophotographic printing machine employs a belt 10, i.e. a charge retentive member, having a photoconductive surface deposited on a conductive substrate. Belt 10 moves in the direction of arrow 16 to advance successive portions thereof sequentially through the various processing stations disposed about the path of movement thereof. Belt 10 is entrained about drive roller 20, tensioning roller 18 and stripping roller 22. Motor 23 rotates roller 20 to advance belt 10 in the direction of arrow 16. Roller 20 is coupled to motor 23 by suitable means such as a belt drive.

Initially successive portions of belt 10 pass through charging station A. At charging station A, a corona generating device, indicated generally by the reference numeral 24, charges the belt 10 to a selectively high uniform electrical potential, preferably negative. Any suitable control, well known in the art, may be employed for controlling the corona generating device 24.

Next, the charged portions of the photoconductive surface are advanced through exposure station B. At exposure station B, the uniformly charged photoconductive surface or charge retentive surface is exposed to a laser based raster output scanning device 25 which causes the charge retentive surface to be selectively discharged in accordance with the output from the scanning device 25. Preferably, the scanning device is a three level laser Raster Output Scanner (ROS). The output scanning device 25 is driven by an input signal from an electronic subsystem (ESS) 27, which would serve as the interface between the device 25 and an input signal generator (not shown). Thus, in this embodiment, the photoconductive surface, which is initially charged to a high charge potential, is discharged image wise in the background (white) image areas and to near zero or ground potential in the highlight (i.e. color other than black) color parts of the image.

At development station C, a magnetic brush development system, indicated generally by the reference numeral 30 advances developer materials into contact with the electrostatic latent images. The development system 30 comprises first and second developer units 32 and 34. Preferably, each magnetic brush developer units includes a pair of magnetic brush developer rollers mounted in a housing. Thus, developer unit 32 contains a pair of magnetic brush rollers 35, 36 with developer unit 34 containing a pair of magnetic brush rollers 37, 38. Each pair of rollers advances its respective developer material into contact with the latent image. Appropriate developer biasing is accomplished via power supplies 41 and 43 electrically connected to respective developer units 32 and 34.

Color discrimination in the development of the electrostatic latent image is achieved by moving the latent image recorded on the photoconductive surface past two developer units 32 and 34 in a single pass with the magnetic brush rolls 35, 36, 37 and 38 electrically biased to voltages which are offset from the background voltage, the direction of offset depending on the polarity of toner in the housing. The first developer unit 32, in the direction of movement of belt 10 as indicated by arrow 16, develops the discharged image areas of the photoconductive surface. This developer unit contains, for example, red developer material 40 having triboelectric properties such that the red toner is driven to the discharged image areas of the latent image by the electrostatic field between the photoconductive surface and the electrically biased developer rolls, which are electrically connected to a bias power supply 41. Conversely, the second developer unit 34, in the direction of movement of belt 10 as indicated by arrow 16, develops the highly charged image areas of the latent image. This developer unit contains black developer, for example, material 42 having a triboelectric charge such that the black toner is urged towards highly charged areas of the latent image by the electrostatic field existing between the photoconductive surface and the electrically biased developer rolls in the second developer unit which are connected to a bias power supply 43. Further, the first and second developer units 32 and 40 have bead removal devices 44 and 46 disposed therein and augers 47 for mixing and charging the developer material.

A sheet of support material 58 is moved into contact with the toner image at transfer station D. The sheet of support material is advanced to transfer station D by conventional sheet feeding apparatus, not shown. Preferably, the sheet feeding apparatus includes a feed roll contacting the uppermost sheet of a stack copy sheets. Feed rolls rotate so as to advance the uppermost sheet from stack into a chute which directs the advancing sheet of support material into contact with the photoconductive surface of belt 10 in a timed sequence so that the toner powder image developed thereon contacts the advancing sheet of support material at transfer station D.

Because the composite image developed on the photoreceptor consists of both positive and negative toner, a negative pre-transfer corona generating device 56 is provided to condition the toner for effective transfer to a substrate using positive corona discharge.

Transfer station D includes a corona generating device 60 which sprays ions of a suitable polarity onto the backside of sheet 58. This attracts substantially simultaneously the black and non-black portions of the toner powder image from the belt 10 to sheet 58. After transfer, the sheet continues to move, in the direction of arrow 62, onto a conveyor (not shown) which advances the sheet to fusing station E.

Fusing station E includes a fuser assembly, indicated generally by the reference numeral 64, which permanently affixes the transferred powder image to sheet 58. Preferably, fuser assembly 64 comprises a heated fuser roller 66 and a pressure roller 68. Sheet 58 passes between fuser roller 66 and pressure roller 68 with the toner powder image contacting fuser roller 66. In this manner, the toner powder image is permanently affixed to sheet 58. After fusing, a chute, not shown, guides the advancing sheet 58 to a catch tray, also not shown, for subsequent removal from the printing machine by the operator. It will also be understood that other post-fusing operations can be included, for example, binding, inverting and returning the sheet for duplexing and the like.

After the sheet of support material is separated from the photoconductive surface of belt 10, the residual toner particles carried by the non-image areas on the photoconductive surface are charged to a suitable polarity and level by a preclean charging device 72 to enable removal therefrom. These particles are removed at cleaning station F. The vacuum assisted, electrostatic, fur brush cleaner unit 70 is disposed at the cleaner station F. The cleaner unit has two fur brush rolls that rotate at relatively high speeds which creates mechanical forces that tend to sweep the residual toner particles into an air stream (provided by a vacuum source), and then into a waste container.

Subsequent to cleaning, a discharge lamp or corona generating device (not shown) dissipates any residual electrostatic charge remaining prior to the charging thereof for the next successive imaging cycle.

It is believed that the foregoing description is sufficient for purposes of the present application to illustrate the general operation of an electrophotographic printing machine incorporating the development apparatus of the present invention therein.

The embodiments of the present invention illustrated within this application will now be further discussed with reference to FIG. 2 which shows a developer unit 34. Developer rollers 37 and 38 of the developer unit 34 are substantially identical to one another so only developer roller 37 will be described.

Continuing with the conventions used to illustrate electrographic printing machines, developer roller 37 advances, for example, the black developer material, including both toner and carrier bead, so that the toner will develop the electrostatic latent image recorded on the photoconductive surface of belt 10. Developer roller 37 is electrically biased so that the highly charged image areas of the latent image attract toner thereto. Developer roller 37 includes a non-magnetic tubular member or sleeve 80 preferably made from aluminum having the exterior surface thereof roughened. Sleeve 80 rotates in the direction of arrow 82. A magnet assembly 84 is mounted interiorly of roller 50 and spaced therefrom. Magnet assembly 84 is stationary and positioned to attract the developer material to the lower exterior circumferential surface of sleeve 80. In this way, as sleeve 80 rotates in the direction of arrow 82, beads are attracted to the exterior circumferential surface by the pick-up magnet 90 which, in this example is oriented with a North (N) magnetic polarity. Thus, beads with toner triboelectrically attracted thereto are magnetically attracted to the sleeve 80 which rotates to mechanically transport developer material (beads and toner) into the development zone 92.

Specifically, the beads attracted to the sleeve 80 by the pickup magnet 90 magnetically attach to the sleeve. Then, the magnetic fields from the so-called transport pole 94, which in this example has a south magnetic polarity urge the continued adherence of the beads to the roller. As the beads continue to adhere to the rotating sleeve 80, the carriers pass through the magnetic field of the so-called "trim-pole" 96 which is used in conjunction with a trim blade or bar (not shown) to regulate or trim the amount of developer material passing to the development zone 92. Magnet assembly 84 is positioned so that two small magnetic poles 98 and 100 of the same polarity are located substantially in the center of the development zone. The magnetic poles on magnets 98 and 100 are located opposed from the photoconductive surface in the region of the gap between sleeve 80 and surface 10.

As the carrier and remaining toner pass the development zone, the bead carryout pole or magnet 102 acts to strongly attract the beads to the sleeve 80. But, as the roller continues to rotate, the beads reach an area 104, where the gravitational force and the centrifugal forces generally overcome the magnetic attraction holding the beads to the roller. This area 104 is often referenced as the bead release zone or point.

As is well known, the placement of two identical polarity oriented magnets adjacent one another results in a magnetic field which has no field reversal and thus always has some potential within finite distances. In roller 37, this condition is present between magnets 90 and 102. Beads could remain on the sleeve 80 past the release area 104, if the gravitational and centrifugal forces are insufficient to overcome the magnetic force on a particular bead. This occurrence causes a reduction in toner delivered to the photoconductive surface and could affect print quality. Of greater concern is the reverse operation of the developers when the sleeves are to be free of developer material. The orientation of the these magnets urges developer material (i.e., carriers with toner) to be attracted to the sleeve 80 and for some beads to be magnetically bound to the sleeve 80 and pass through the development zone 92. Applicants have found that placing ferromagnetic shunt 106 adjacent magnet 102 have overcome these problems. The shunt 106 is oriented to attenuate the magnets field between magnet 102 and magnet 90 to thereby reduce the attraction of bead carriers to the sleeve 80 in the zone 104. The positioning of the shunt 106 not only improves bead carrier release in normal operation, but reduces the number of beads adhering to the sleeve 80 during reversed rotation of the developers. The magnetic field strength at the bead release zone 104 is still not zero, but it is substantially reduced to effect these advantages.

Applicants have used cold rolled steel with a permeability of at least 1500 or greater of and at least approximately 1 to 3 mm thick with a thickness of between 1.5 mm and 1.6 mm being preferred for forming these shunts. Applicants believe that the permeability of the material used may vary approximately between 180 and 2000 with 1000 a preferred minimum. Generally, the shunt 106 has first and second sides disposed around the magnet 102 to provide the discussed features. The magnets of the unit 84 are generally formed of a rubber or plastic material and embedded in foam in a standard fashion. The magnetic units 84 within the sleeves 80 can be formed in a variety of manners including, by way of example, that disclosed in U.S. Pat. Nos. 4,517,719 and 4,640,808.

Figure 2:
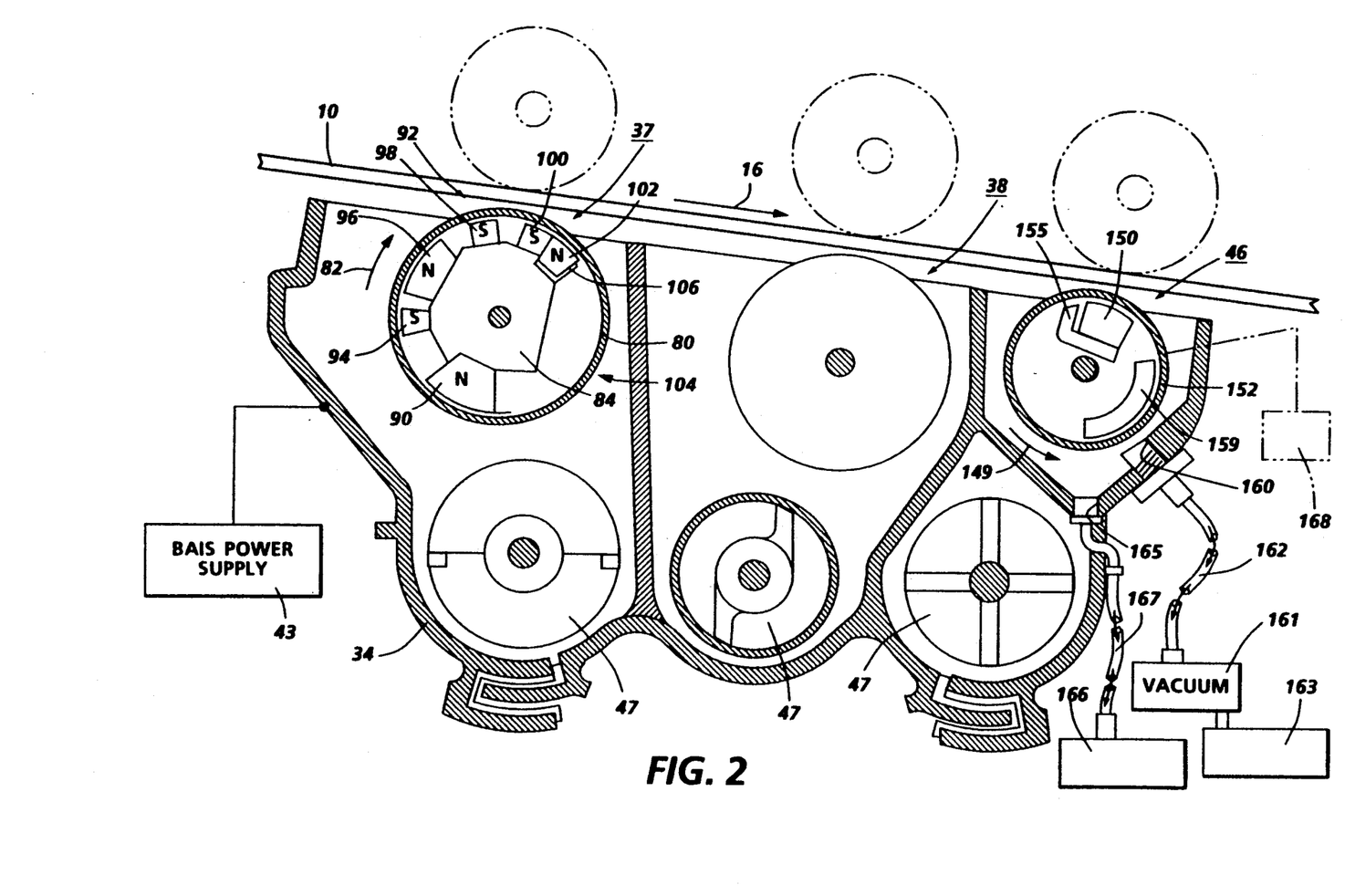
FIG. 2 is an elevational view showing a developer unit and a portion of the photoconductive surface of the FIG. 1 printing machine.

Continuing to reference FIG. 2, the developer unit 34 is shown with a bead removal device 46. The bead removal device 46 generally rotates in the direction indicate by arrows 149 (i.e., opposite the direction of the developer rollers 37 and 38) are shown with magnet 150 disposed in a fixed relationship with the belt 10. The magnet 150 is stationary and disposed within rotating sleeve 152. Shunt 155 is disposed within the sleeve 152 to shape the magnetic fields generated by the magnet 150 in selected directions. Further, shunt 159 is positioned in conjunction with the magnet 150 and shunt 155 so the magnetic field from the magnet is minimized along the sleeve 80 in all but those directions generally radiating toward the belt 10. A vacuum port 160, positioned in the wall of the housing of the development unit 34, is connected to a vacuum source 161 via a conduit 162 to urge release of materials retained on the sleeve 80 and deposit of such materials in a sump 163. A second port 165 is also positioned in the housing to allow materials not passing through the vacuum port 160 to sump 163 to pass to the sump 166 through conduit 167. It will be recognized that in many applications the sumps 163 and 166 can be combined into a single sump so that materials passing through ports 161 and 165 ultimately end in the single sump and/or that both ports 160 and 165 could be connected to the vacuum source 161.

The shunts 155 and 159 of BRD 46 are preferably formed of a ferromagnetic material (e.g. cold rolled steel with a thickness greater than approximately 1 mm) with a preferred thickness of between approximately 1.5 mm and 1.6 mm. The magnet 150 are ordinarily so-called rare earth magnets. The magnet and shunts may be held in place by foam in a fashion similar to that discussed with magnetic units 84. Applicants have also discovered that in many instances application of an AC or DC voltage from an AC or DC power source 168 to the sleeve 152 of the bead removal device 146 substantially increases the efficiency of such devices. Applicants have found that the voltage applied should be between 1000 and 3000 volts peak to peak AC or between 500 and 1500 volts DC and, preferably, approximately 2000 volts of a low amperage AC voltage or 1000 volts DC. Nevertheless, Applicants have also found that application of such a voltage to the BRD sleeve 152, which in this case is electrically isolated from the developer housing 34, is of limited value. Over time the buildup of material including toner along the sleeve fouls it and minimizes its effectiveness. Thus, Applicants have also found it appropriate to include an air knife or vacuum means as embodied in the port 160 and vacuum source 161 to assist removal of developer material including bead carriers from the housing.

Further, as will be appreciated, except for the portions of the shell proximate the photoconductive surface and the portions immediately adjacent thereto the magnetic field strength along the bead removal device's sleeve 152 is minimized by the disclosed arrangement. The optimal arrangement is dependent, in part, however, upon the characteristics of the developer material and ambient conditions. Generally, Applicants have found that the shunt 159 should be formed of cold rolled steel with a permeability of substantially 1500 with a thickness of at least 1 mm or more. Applicants have also found that the forming of the shunt 159 as arc shunts with a radius proportional to the BRD's shell provides a greater effectiveness, although ferromagnetic strips have been employed. Generally then, with the disclosed arrangement of shunts and magnets, beads will be attracted to the BRD from the belt 10 and then deposited in a sump or returned to the reservoir of developer material 42.

Applicants have further found that overall performance of the BRD is improved, if the captured beads are directed to a sump for removal rather than returned to the developer material in the developer housing 34 for reuse. It appears that recirculation of the bead carriers captured by the BRD into the developer housing tend to be prone to carryout. Thus, in the preferred embodiment, the sump means as embodied in sump 163 and 166 is provided for the developer material captured by the BRD, including particularly bead carriers. Nevertheless, satisfactory results have also been achieved with a recirculating system.

Figure 3:
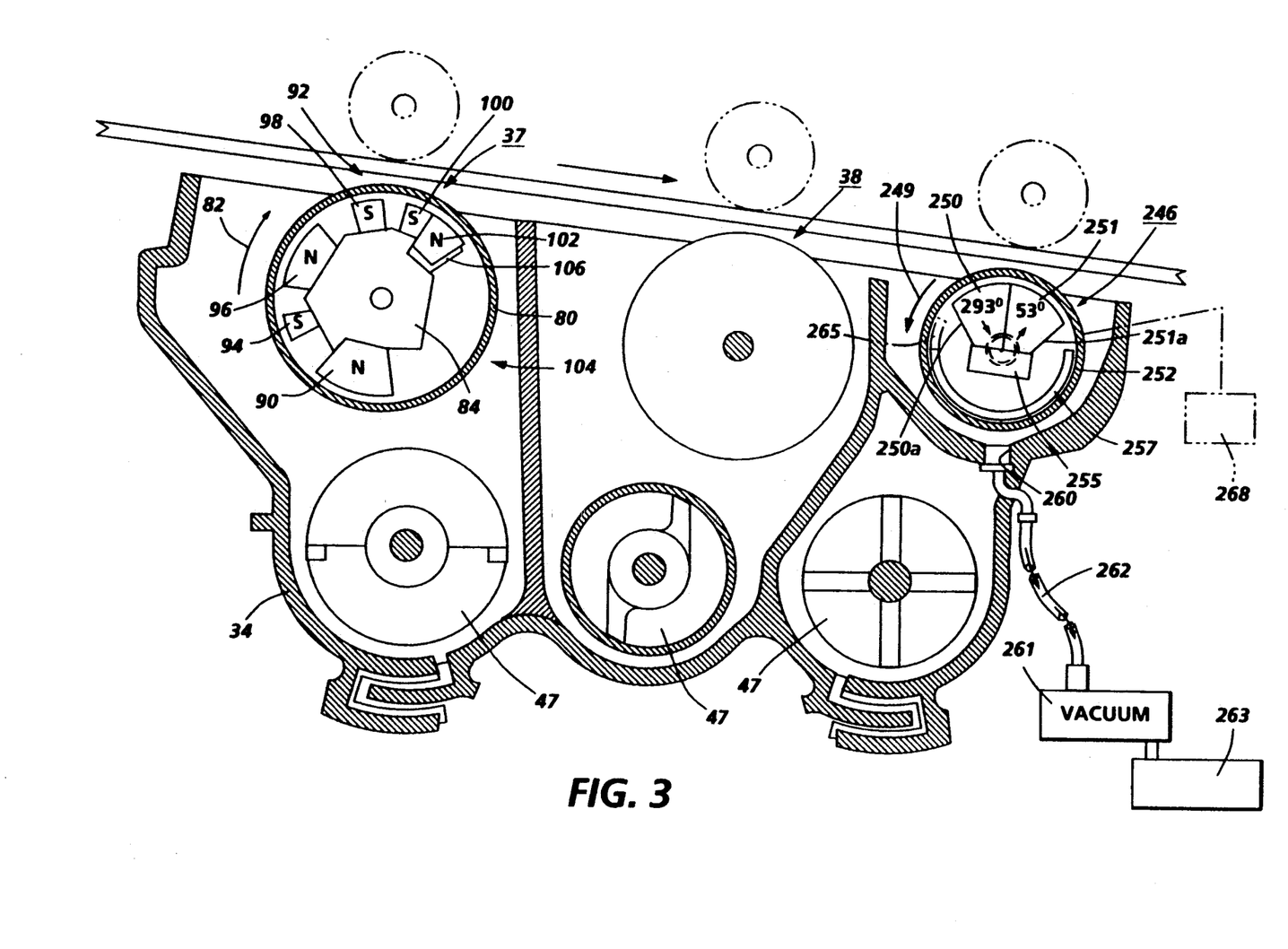
FIG. 3 is an elevational view showing an alternative embodiment of one of the developer rollers used in one of the developer unit of the FIG. 1 printing machine.

FIG. 3 is a view of a developer unit similar to that of FIG. 2 and in accordance with the present invention. Substantially identical portions of these referenced figures are commonly numbered for ease of understanding. For example, the developer rollers 35 and 37 of FIG. 3 is identical to those of FIG. 2. The bead removal devices 246 as shown with the developer unit 34 of FIG. 3 is not, however, identical to the device 46 of FIG. 2. Nevertheless, similar to the embodiment of FIG. 2, the bead removal devices 246 are rotationally driven by a motor, not shown and the preferred rotational direction is opposite the rotation of the developer rollers 37 and 38 as indicated by arrow 249. The magnetic field generating means of the BRD 246, however, comprises two magnets, magnets 250 and 251, disposed in a fixed relationship with the belt 10. The magnets 250 and 251, which are, thus, stationary within the roller housing sleeve 252 which rotates. Shunt 255 is disposed within the sleeve 252 to shape the magnetic fields generated by the magnets 250 and 251 in selected directions. Further, shunt 257 is positioned in conjunction with the magnets 250 and 251 and shunt 255 so the magnetic field form the magnets is attenuated in all but those directions generally radiating toward the belt 10.

Shunts 255 and 257 of the bead removal devices 246 are preferably formed of a ferromagnetic material (e.g., low carbon cold rolled steel with a thickness greater than 1 mm and preferably approximately 1.6 mm thick). The permeability of the material used is approximately 1000 and preferably between 180 and 2000. The magnets 250 and 251 are of substantially opposite polarity relative to their positioning within the housing 252. The magnets are preferably a Neodymium Iron Boron alloy (NIB) available from Delco-Remy (a division of General Motors Corporation). It will be appreciated that other materials can be used to accomplish substantially the same results. The magnets and shunts may be held in place by foam in a fashion similar to that discussed with magnetic unit 84, previously.

As stated above, the magnets 250 and 251 are arranged in approximate opposite polarity orientation. That is, one magnet has a north pole of approximately opposite orientation of the north pole of the other so that the magnets 250 and 251 do not repel but rather attract each other. Applicants have found that the maximum force across the nip between the shell and the surface is yielded by magnetic vectors of the two magnets being offset between approximately 140° to 100° and preferably 120° (See FIG. 3, wherein the north poles of magnet 250 and 251 are at 53° and 293°, respectively, so that in the example only 60° separate the opposite poles adjacent the surface 10.) Further, it has been found that magnetic fields radiating in directions away from the surface 10 in the shown configuration are minimized when the walls 258 and 259 of magnets 250 and 251 are formed approximately parallel to the magnetic polar axis of the magnets 250 and 251, respectively.

Applicants have discovered that in some cases, arc shunt 257 should extend in a direction further toward the photoconductive surface 10. It has been found that, due to the proximity of the developer rollers 37 and 38 to bead removal device 246 the magnetic fields between them can inhibit and affect their respective functions. Generally, in such cases the shunt 257 would extend in an arc between 5° and 20°, as shown by the phantom section 265. This and the shaped walls 250 and 251 substantially eliminate magnetic interference or cross talk between the bead removal device and developer roller. Applicants have also discovered that in many instances application of an AC or DC voltage to the sleeve 252 from an AC or DC power source 268 substantially increases the bead removal efficiency of the bead removal device 246. Applicants have found that the voltage applied should be between 1000 and 3000 volts peak to peak AC or 500 and 1500 volts DC and, preferably, approximately 2000 volts of a low amperage AC voltage or 1000 volts of a DC voltage. Applicants have also provided a vacuum air knife to assist release of bead carriers from the sleeve 252 which includes a vacuum port 260 connected to a vacuum source 261 via conduit 262 to transport material from the sleeve to a sump 263.

Applicants have found that the vacuum port 160 and vacuum port 260 should be between 0.25 and 1.5 mm away from the sleeve 152 and sleeve 252 of the BRD 46 and 246 in FIGS. 2 and 3, respectively, with 0.75 mm being preferred. Further, Applicants have used a flow rate of approximately 0.5 liters/sec into a nozzle which is 2 mm wide and approximately 360 mm long. Applicants believe that an appropriate flow rate would be between 0.25 and 1.5 liters/sec into a nozzle between 0.75 and 4 mm wide. Applicants have avoided the air flow affecting the development of the image on the surface 10 by positioning the vacuum port close to the sleeve and not substantially closing the air passage around the sleeve adjacent the surface 10.

Figure 4:
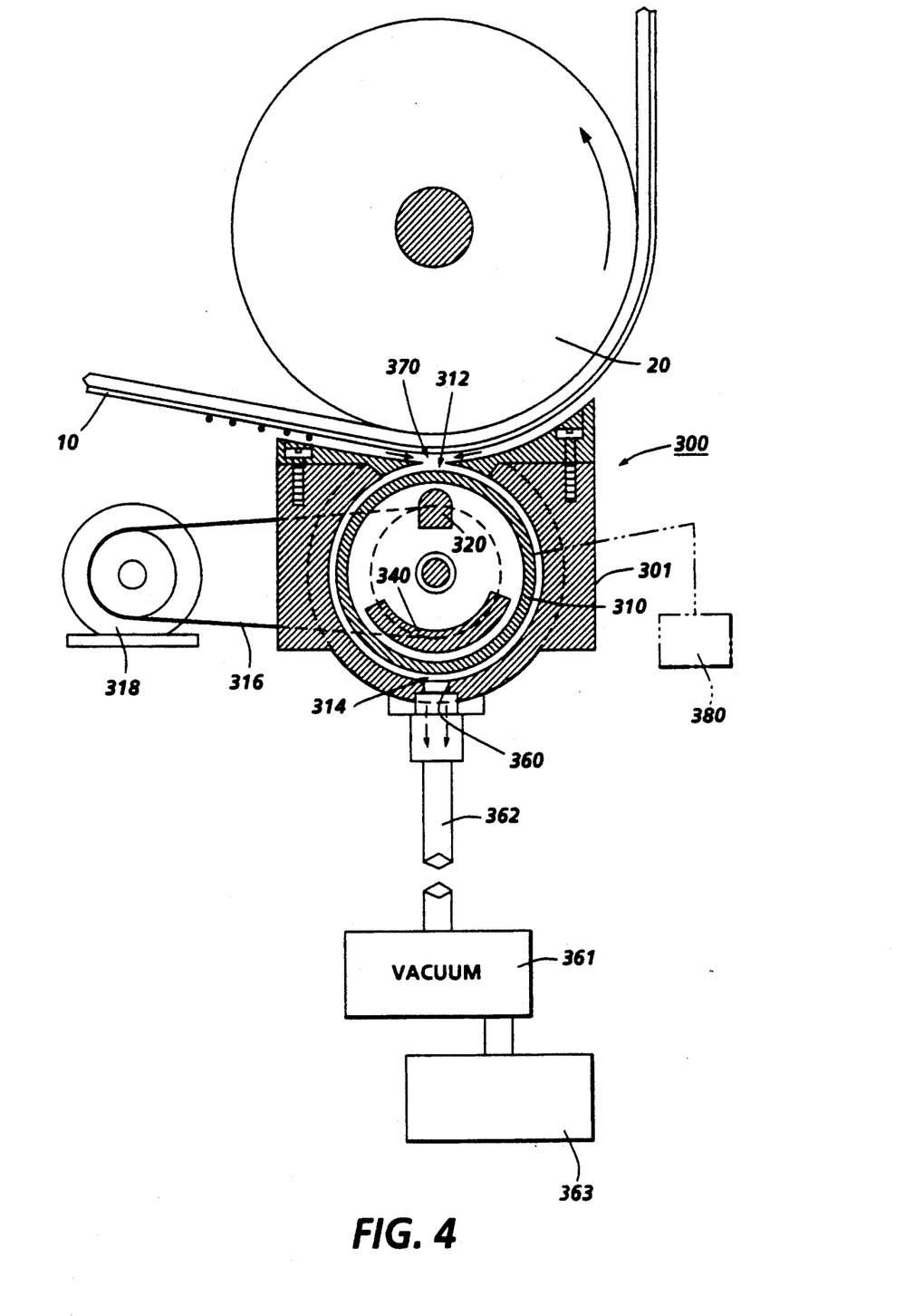
FIG. 4 is an elevational view showing a bead removal device and a portion of the FIG. 1 printing machine.

Another embodiment of the present invention is shown in FIG. 4. Specifically, a magnetic air bead pick off device 300 positioned downstream of the developer housing. Applicants believe that use of such a device improves efficient operation of an electrophotographic printing machine, including, particularly, by substantially reducing the number of beads carrying through to the transfer station and thus, substantially reduces bead carrier deletions being visible in produced copies. The magnetic air bead pick off device is shown with an outer housing 301 which has an inner rotating sleeve 310 mounted therein. The sleeve 310 is formed of a non-magnetic material, such as aluminum, and it is preferred that the outer surface is roughened. The sleeve is driven by a rotatable motive means such as the belt 316 and motor 318.

A magnet 320 and a shunt 340 are fixedly mounted within the sleeve 310 which is mounted for rotation around them. The magnet 320 is positioned in the sleeve 310 so that a pick up zone 312 is defined on the shell of the sleeve 310 adjacent the surface of the belt 10. The positioning of the shunt 340 and the magnet 320 define a release area 314 where the magnetic field strength is generated by the magnet 320 along the sleeve 310 is minimized or attenuated by the shunt 340. It will also be recognized and understood that the magnet 320 and shunt 340 can be replaced by a set of magnets and shunts similar to that disclosed in the BRD 246 of FIG. 3.

The vacuum portion of the combination magnetic air bead pick off device 300 includes a vacuum source 361, a vacuum port 360 to receive captured beads and other materials within the inner walls of the housing 301; an air conduit 362 connecting the source 361 with the port 360, and a sump 363 for receiving materials passing from the inner walls of the house in 301 through the port 360. The walls of the housing 301 form a venturi thin plate nozzle 370 adjacent the surface 10 opposite the magnet 320 so that the air flow generated through the nozzle by the vacuum source and the magnetic field generated by the magnet 320 attract materials both on and near the surface 10 toward the pickup zone. Thus, loose toner, free toner, and agglomerate materials are urged toward the inlet nozzle.

Applicants believe that in employing the bead pick off device of this invention such as that disclosed in FIG. 4, the nozzle 370 should be disposed between 0.25 and 1.75 mm away from surface 10 with 0.75 mm perferred. Applicants also believe that the nozzle 370 should also be between 0.25 and 3 mm wide with a flow rate through the nozzle that is between 0.1 and 2.5 liters/sec. Applicants have used a nozzle 370 that is approximately 1 mm wide in the direction of belt rotation and 360 mm long with an air flow through the nozzle of 0.2 ltrs/sec. Applicants believe that variations in these preferred parameters can be made according to the details and conditions of the printers machine and material in which the device is used as well as the ambient conditions for the relevant parameters. It will be further understood that the described embodiment of FIG. 4 may be placed, as appropriate, along the photoconductive surface between a developer unit and a transfer station. It will be noted that in certain applications, the applying of an AC or DC bias to the sleeve 310 by an AC or DC power source 380 may enhance the performance of the device 300, as previously discussed with respect to the bead removal devices 46 and 246 of FIGS. 2 and 3, respectively.

It will be understood that the present magnetic vacuum bead pick off devices of this invention, as described in illustrative detail in conjunction with FIGS. 2, 3, and 4 can be used singularly or in conjunction with the other embodiments of this invention to be effective, as necessitated by the constraints of the applications in which employed. The present invention, as previously indicated is not limited to use in single-pass highlight color electrophotographic printing machines but would be useful in single, two-pass and multi-pass electrographic printing machines generally. Applicants have found satisfactory results with the employment of two embodiments of the invention concurrently (e.g., a magnetic bead pick off device in the developer housing itself and another magnetic air bead pick off device position downstream therefrom prior to the transfer station.). But in many circumstances, as indicated, employment of a single embodiment of the present invention achieves the aims and goals of this Application.

In recapitulation, the latent image recorded on the photoconductive surface has areas imaged according to its charge state. The developer unit, in the direction of movement of the photoconductive surface, develops the imaged areas of the latent image with toner. The developer unit has at least one developer roller which has magnetic means positioned therein for generating a magnetic field extending therefrom and shaped by the positioning of magnets and magnetic field shaping shunts. Further, the BRD is provided with an outer roller housing, a fixed magnet which operates to attract carriers adhering to the photoconductive surface to the BRD roller housing and deposit the carriers in a sump, a shunt to shape the fields of the magnet to encourage release of carriers into the sump, and an air flow generator for generating an air flow which also encourages release of material from the roller housing and deposit of the carriers in a sump. An AC or DC power source connected to the BRD roller housing further improves the performance of the BRD under appropriate conditions.

It is, therefore, apparent that there has been provided in accordance with the present invention, a BRD for use in an electrophotographic printing machine that fully satisfies the aims and advantages hereinbefore set forth. While this invention has been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of the appended claims.

We claim:

1. An apparatus for developing a latent image recorded on a moving photoconductive surface to form a developed image on the photoconductive surface for transfer to a sheet at a transfer station comprising:
   magnetic means, generating a magnetic field, for attracting and moving magnetic carrier beads having toner particles adhering triboelectrically thereto to a development zone proximate to the photoconductive surface so that the latent image attracts toner particles from the carrier beads thereto;
   magnetic pick off means, positioned adjacent the photoconductive surface intermediate the transfer station and the development zone for removing magnetic carrier beads adhering to the photoconductive surface; and
   vacuum means for removing magnetic carrier beads adhering to said magnetic pick off means.

2. The apparatus of claim 1, wherein said magnetic pick off means includes a rotatably mounted non-magnetic tubular member, means for rotating said tubular member and a magnetic unit disposed stationarily, within said tubular member for generating a second magnetic field which defines a pick off area on said tubular member so that the bead carriers are attracted and adhere to said tubular member in the pickup area.

3. The apparatus of claim 2, wherein said magnetic pick off means further includes a shunt for minimizing the magnetic field generated by said magnetic unit to define a release area on said tubular member so that the bead carriers adhering to said tubular member are released therefrom.

4. The apparatus of claim 3, further comprising a housing having at least said magnetic pick off means disposed therein, said housing defining an input port adjacent the release area with said vacuum means being coupled to the input port.

5. The apparatus of claim 4, wherein said shunt is mounted stationarily within said tubular member and is positioned substantially between said magnetic unit and the release area defined on said tubular member.

6. The apparatus of claim 5, wherein said shunt comprises a strip of ferromagnetic material.

7. The apparatus of claim 4, wherein said housing defines an aperture adjacent the photoconductive surface so that beads attracted to said magnetic pick off means enter said housing through the aperture therein.

8. The apparatus of claim 7, wherein the aperture in said housing comprises a venturi nozzle so that the flow generated by said vacuum means between said housing and the photoconductive surface urges bead carriers therebetween toward said nozzle.

9. A method for developing a latent image recorded on a moving photoconductive surface to form a developed image on the photoconductive surface for transfer to a sheet at a transfer station, comprising the steps of:
   generating a magnetic field for attracting magnetic carrier beads having toner particles adhering triboelectrically thereto, and moving the magnetic carrier beads and toner particles to a development zone proximate to the photoconductive surface so that the latent image attracts toner particles from the carrier beads thereto;
   generating a second magnetic field with a magnetic pick off device positioned adjacent the photoconductive surface intermediate the transfer station and the development zone for removing magnetic carrier beads adhering to the photoconductive surface; and
   generating an aeriform fluid flow to remove magnetic carrier beads adhering to the magnetic pick off means.

10. The method of claim 9, further comprising the step of electrically biasing the magnetic pick off device to attract toner thereto, wherein said step of generating the aeriform fluid comprises removing toner from the magnetic pick off device.

11. The method of claim 10, wherein the step of generating the aeriform fluid flow includes moving bead carriers, on or adjacent the magnetic pick off device to a location remote therefrom.

12. An apparatus for removing magnetic carrier beads from a developed image formed on a moving photoconductive surface at a developing zone and adapted to be transferred to a sheet at a transfer station, comprising:
   a first magnetic bead pick off device positioned proximate a downstream portion of the developing zone in the direction of movement of the photoconductive surface for removing magnetic carrier beads adhering to the photoconductive surface;

a second magnetic bead pick off device intermediate said first bead pick off device and the transfer station;

an air flow generator for generating an air flow from the photoconductive surface toward said second magnetic bead pick off such that contaminants proximate the photoconductive surface are attracted to said second magnetic bead pick off device; and a rotating sleeve for supporting said second magnetic bead pick off device therein, said sleeve and the photoconductive surface defining a nip area therebetween; and a housing for supporting and confining said sleeve, said housing defining an aperture in the nip area such that said air flow generator generates an air flow from outside said housing into said housing through the aperture therein such that the air flow and said second magnet attract contaminants proximate the photoconductive surface into said housing.

13. The apparatus of claim 12 wherein said housing is spaced from the photoconductive surface so that the aperture therein provides an air flow controlling nozzle such that said air flow generator produces a high velocity air flow about said sleeve to remove contaminants from said sleeve.

14. The apparatus of claim 13 further comprising magnetic field shapers disposed proximate said first magnetic bead pick off device and said second magnetic pick off device to enhance release of magnetic bead carriers from said first magnetic pick off and said second magnetic pick off devices.

* * * * *